United States Patent
Farmer

[11] Patent Number: 6,123,906
[45] Date of Patent: *Sep. 26, 2000

[54] AIR FRESHENING DEVICE FOR AUTOMOBILES

[76] Inventor: Mike Farmer, 4604 Deerfield Ct., Sioux Falls, S. Dak. 57105

[*] Notice: This patent issued on a continued prosecution application filed under 37 CFR 1.53(d), and is subject to the twenty year patent term provisions of 35 U.S.C. 154(a)(2).

[21] Appl. No.: 08/857,518

[22] Filed: May 16, 1997

Related U.S. Application Data

[63] Continuation-in-part of application No. 08/633,125, Apr. 16, 1996, abandoned.

[51] Int. Cl.⁷ ........................................................ A61L 9/12
[52] U.S. Cl. .............................. 422/124; 422/123; 239/36; D23/366
[58] Field of Search ................................. 422/123, 124; 239/54, 60, 36; 428/905; D23/366, 367, 368

[56] References Cited

U.S. PATENT DOCUMENTS

| | | |
|---|---|---|
| D. 281,102 | 10/1985 | Bush et al. ............................... D23/150 |
| D. 313,274 | 12/1990 | Peterson ................................. D23/369 |
| D. 348,098 | 6/1994 | Patrice ................................... D23/366 |
| D. 365,392 | 12/1995 | Van Gundy et al. ................... D23/369 |
| D. 373,626 | 9/1996 | Dente et al. ........................... D23/366 |
| D. 382,050 | 8/1997 | Hayes .................................... D23/366 |
| D. 417,727 | 12/1999 | Christianson ......................... D23/366 |
| 2,560,681 | 7/1951 | Berkowitz . |
| 2,721,098 | 10/1955 | Mangels . |
| 2,806,315 | 9/1957 | Kalensky . |
| 3,185,394 | 5/1965 | Farrell ...................................... 239/36 |
| 3,733,016 | 5/1973 | Rood . |
| 4,432,938 | 2/1984 | Meetz, Jr. ........................... 422/124 X |
| 4,523,870 | 6/1985 | Spector . |
| 4,582,635 | 4/1986 | Furuuchi et al. . |
| 4,802,626 | 2/1989 | Forbes et al. ............................. 239/36 |
| 4,808,347 | 2/1989 | Dawn ................................ 422/124 X |
| 4,813,344 | 3/1989 | Greif . |
| 4,840,773 | 6/1989 | Wade . |
| 4,892,711 | 1/1990 | Tendick, Sr. ............................ 422/125 |
| 4,903,584 | 2/1990 | Styles . |
| 5,269,723 | 12/1993 | Bender . |
| 5,273,690 | 12/1993 | McDowell ......................... 422/124 X |
| 5,368,822 | 11/1994 | McNeil ................................ 422/124 |
| 5,407,642 | 4/1995 | Lord . |
| 5,422,078 | 6/1995 | Colon .................................... 422/123 |
| 5,478,505 | 12/1995 | McElfresh et al. . |
| 5,527,493 | 6/1996 | McElfresh et al. ................. 422/124 X |
| 5,547,636 | 8/1996 | Vick et al. ............................. 422/124 |
| 5,603,455 | 2/1997 | Lin ............................................ 239/44 |
| 5,762,549 | 6/1998 | Scheuer et al. ....................... 422/124 |
| 5,775,876 | 7/1998 | Walker et al. ..................... 422/124 X |
| 5,833,929 | 11/1998 | Watson et al. ......................... 422/123 |
| 5,932,147 | 8/1999 | Chen .................................. 422/124 X |

*Primary Examiner*—Elizabeth McKane
*Attorney, Agent, or Firm*—Fulwider Patton Lee & Utecht, LLP

[57] ABSTRACT

A device for allowing either perfumed materials or deodorizing materials to the surrounding vehicle known as an air freshener including a clip device holding the material and adapted to be connected to an air vent fin which vents warmed or cooled air into a space. The device is adapted to be inserted into the vent where it will be less intrusive into space outside the vent.

16 Claims, 1 Drawing Sheet

AIR FRESHENING DEVICE FOR AUTOMOBILES

This invention pertains to air fresheners adapted to remove or to cover unpleasant odors in some living space, and is a continuation in part of applicants prior application, Ser. No. 08/633,125, filed Apr. 16, 1996 and now specifically abandoned. It is adapted for use in automotive vehicles or in dwellings and includes a novel clip device adapted to be held in the discharge of a heating or a cooling system.

BACKGROUND AND SUMMARY OF THE INVENTION

In many types of living space, but particularly in the passenger compartment of cars and trucks, there are often unpleasant odors. Such odors as that of stale tobacco smoke or odors of some material being carried in the passenger compartment can be offensive to many people. Often that offensive odor is opposed by use of hanging devices having other perfumes or deodorant material absorbed into the device to be hung in the car. These devices are most often hung from the rear-view mirror or the sun shades in the vehicle.

This invention provides a simple and much more efficient way of distributing the sort of material that is absorbed into the former hanging devices. It also avoids any dangling object which might be distracting to the driver of an automobile. Further, it is inserted to be non-intrusive in outer space.

DESCRIPTION

Figure 1:
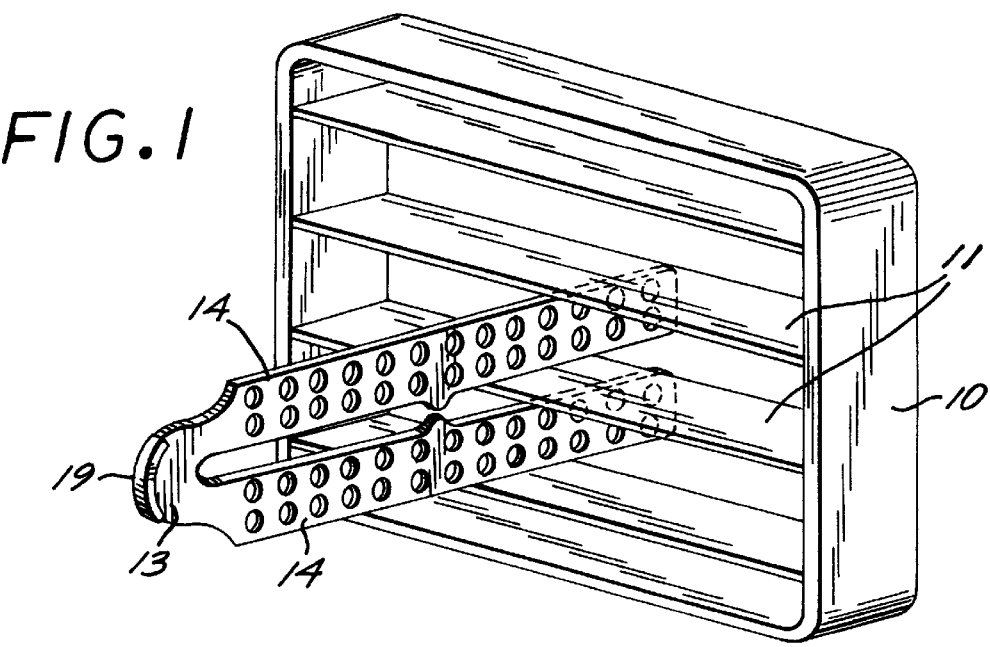
FIG. 1 is a perspective view of the air freshener clip in place on a discharge grill.
Figures 2, 3:
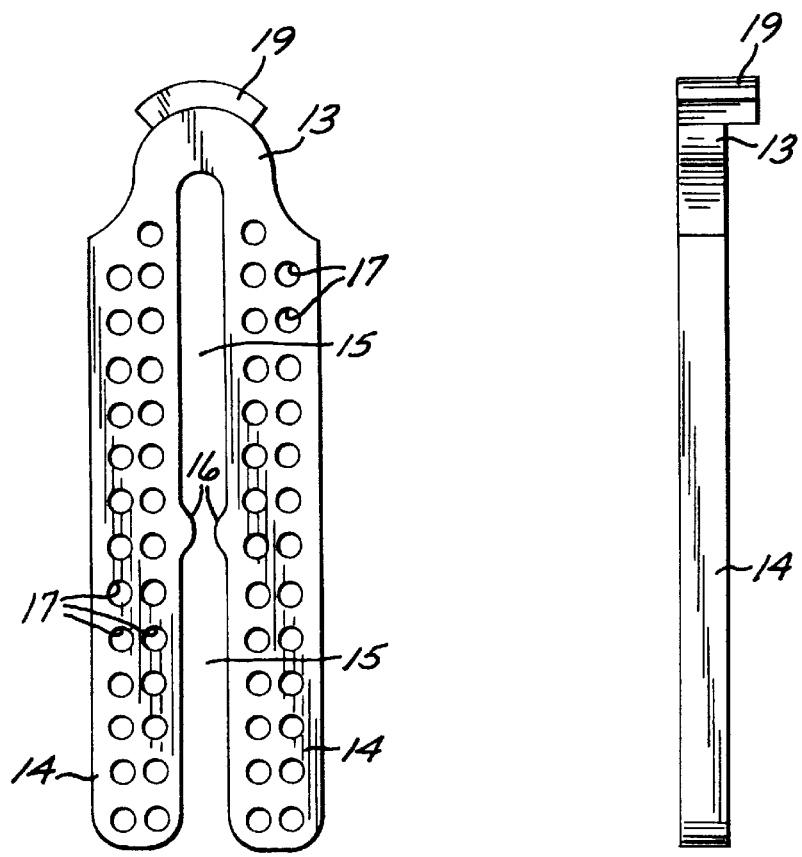
FIG. 2 is a plan view of the clip to an enlarged scale.
FIG. 3 is an edge view of the clip shown in FIG. 2.

Briefly this invention is a clip adapted to carry a deodorant or perfumed material and adapted by its formation to be held directly in the flow of air from a vent whether that air is heated or cooled.

More specifically, and referring to the drawings, the clip is designed principally to be held in a discharge vent 10 of a ventilation system but it may also be adapted to any similar vent of any ventilating mechanism such as a central heater or air conditioner or a room air conditioner or other similar system which has louvers 11 in the discharge.

The clip itself is shaped as a flat sheet of a polypropylene polymer material impregnated at forming with an oil having the desired fragrance. Such materials are generally known and are often used in the form of small cakes for use in urinals in men's public restrooms. In essence the clip is shaped as a fork having a head end 13 and two legs 14. The legs are spaced apart so as to leave spaces 15 between them, but also carry matching, opposite protrusions 16 which are adapted almost to close the spaces 15. Thus, while the legs 14 are wide enough that they cannot easily be spread, there is space enough in the open spaces 15 to receive the louvers 11, of the vent.

The legs fit between the louvers, so that the clip can then be inserted into place. The natural resilience of the material of the clip allows the protrusion to slide over the louvers 11 and may thus hold the clip in place.

Holes 17 are provided to increase the area from which the fragrance impregnated into the polypropylene material will be emitted. If the clip is placed somewhat diagonal to the airflow, the flow of air through these holes will greatly enhance the effectiveness of the device.

For ease in handling, a cross tab 19 may be provided to make placement and removal of the clip easier.

I claim as my invention:

1. An air freshener for mounting to an air grill including parallel louvers spaced apart a predetermined distance to define air passages therebetween and comprising:

a unitary flat stock of fragrance impregnated resilient thermoplastic material configured to form a fork having a length and width, said fork defining parallel tines of a width less than the predetermined distance for receipt in passages disposed on opposite sides of a selected louver;

said tines spaced laterally apart and being sufficiently resilient to be received over the selected louver, said tines being formed with openings spaced along the length thereof for flow of air therethrough for release of fragrance therefrom; and said fork further including a hand grip on the closed end thereof whereby said hand grip may be grasped and said tines flexed to be inserted straddling the selected louver so as to be received in the passages to divide the passages for flow of air on opposite sides of said fork.

2. An air freshener as set forth in claim 1 wherein:
   said tines are wider than they are thick.

3. An air freshener as set forth in claim 1 wherein:
   at least one of said tines includes a protrusion projecting laterally toward said other tine to form a stop to be registered behind said selected louver.

4. An air freshener as set forth in claim 1 wherein:
   said tines are formed with a uniform thickness defining planar surfaces on the opposite sides thereof.

5. An air freshener as set forth in claim 4 wherein:
   said fork includes a portion on the closed end thereof projecting laterally of the extended plane of one side of said tine to form said hand grasp.

6. An air freshener as set forth in claim 1 wherein:
   said fork includes a transverse tab defining said hand grasp.

7. An air freshener as set forth in claim 1 wherein:
   said tines are formed with respective widths greater than one-half said predetermined distance.

8. An air freshener as set forth in claim 1 wherein:
   said tines are formed with respective widths sufficient to project substantially across said predetermined distance defined by the spacing between said louvers.

9. An air freshener as set forth in claim 1 wherein:
   said fork is constructed with said tines having confronting edges normally spaced apart, at least one of said tines being formed on its confronting edge with a stop projecting laterally toward the other of said tines but terminating short of said confronting edge of said other of said tines to leave a space.

10. An air freshener as set forth in claim 9 wherein:
    said other of said tines includes a stop projecting laterally of said other of said tines toward the first mentioned stop but terminating short thereof to leave a space between said stops.

11. An air freshener as set forth in claim 1 wherein:
    said fork is formed from a sheet of polymer material.

12. An air freshener as set forth in claim 1 wherein:

said holes project through the thickness of said tines.

13. An air freshener for mounting to an air grill including parallel louvers spaced apart a predetermined distance to define air passages therebetween and comprising:

- a unitary flat stock of fragrance impregnated resilient material configured to form a fork having a length and width, said fork defining parallel tines of a width less than said predetermined distance for receipt in passages disposed on opposite sides of a selected louver;
- said tines spaced laterally apart and being sufficiently resilient to be received over the selected louver; and
- said fork further including a hand grip on the closed end thereof whereby said hand grip may be grasped and said tines flexed to be inserted straddling the selected louver so as to be received in the passages to divide the passages for flow of air on opposite sides of said fork.

14. An air freshener for mounting to an air grill including parallel louvers spaced apart a predetermined distance to define air passages therebetween and comprising:

- a unitary flat stock of fragrance impregnated resilient material configured to form a fork having a length and width, said fork defining parallel tines of a width less than said predetermined distance for receipt in passages disposed on opposite sides of a selected louver;
- said tines spaced laterally apart and being sufficiently resilient to be received over the selected louver, at least one of said tines further including a stop spaced from the closed end of said fork a distance greater than the width of the selected louver and projecting toward the other said tine for receipt of the selected louver between said tine behind said stop; and
- said fork further including a hand grip on the closed end thereof whereby said hand grip may be grasped and said times flexed to be inserted straddling the selected louver so as to be received in the passages to divide the passages for flow of air on opposite sides of said fork.

15. A method of making an air freshener for mounting over a louver of an air grill having parallel louvers spaced apart a predetermined distance and including:

- selecting a polyethylene material;
- impregnating said polyethylene material with a fragrance;
- forming said fragrance impregnated polyethylene material in the shape of a fork having a pair of resilient parallel tines projecting longitudinally and spaced so as to be fitted over a selected louver and formed with a width to project laterally in the spaces on the respective opposite sides of such louver for receiving air flow along the opposite sides thereof,
- forming said tines with openings spaced along the length thereof for enhancing air flow for carrying the impregnated fragrance into the air flow; and
- forming the fork on the closed end with a hand grasp element.

16. The method set forth in claim 15 that includes:

in the step of forming said tines, forming said tines with said openings projecting through the body of said tines.

* * * * *